United States Patent [19]

Albright et al.

[11] 4,160,795

[45] Jul. 10, 1979

[54] DURABLE FLAME RETARDANT FOR POLYESTER TEXTILE MATERIALS

[75] Inventors: James A. Albright; Richard R. Nicholson, both of Ann Arbor, Mich.

[73] Assignee: Velsicol Chemical Corporation, Chicago, Ill.

[21] Appl. No.: 869,084

[22] Filed: Jan. 13, 1978

[51] Int. Cl.[2] .......................... C07F 9/165; C07F 9/08

[52] U.S. Cl. ................................ 260/937; 260/927 R

[58] Field of Search ............................ 260/937, 927 R

[56] References Cited

U.S. PATENT DOCUMENTS

| | | | |
|---|---|---|---|
| 4,012,466 | 3/1977 | Wang et al. | 260/937 |
| 4,049,617 | 9/1977 | Albright | 260/937 |

*Primary Examiner*—Natalie Trousof

*Assistant Examiner*—Robert C. Whittenbaugh

*Attorney, Agent, or Firm*—Robert M. Phipps; Howard J. Greenwald

[57] ABSTRACT

Disclosed are novel compounds of the formula:

$$\left[ \begin{array}{c} Z\,CH_2 \\ Z\,CH_2 \end{array} \!\!>\! C \!<\! \begin{array}{c} CH_2-O \\ CH_2-O \end{array} \!\!>\! \overset{Y}{\overset{\|}{P}}-O-CH_2 \right]_m -C \begin{array}{l} (CH_2X)_a \\ (CH_2X')_b \\ (CH_2X'')_c \end{array}$$

wherein each Z is independently selected from the group consisting of hydrogen and halogen; Y is oxygen or sulfur; n is an integer of from 1 to 3; a, b, and c are integers of from 0 to 1; $n+a+b+c=4$; and wherein X, X', X'' are independently selected from the group consisting of hydrogen, halogen, alkyl of 1 to about 8 carbon atoms and —OC(O)R, provided that at least one of said X, X', X'' substituents is —OC(O)R, and R is independently selected from the group consisting of alkyl of 1 to about 18 carbon atoms, haloalkyl of 1 to about 18 carbon atoms, alkoxyalkyl of from 1 to about 18 carbon atoms, aryl of from 6 to about 18 carbon atoms, and haloaryl of from about 6 to about 18 carbon atoms.

The above compounds may be topically applied to polyester-containing textile materials in order to flame retard them; and the materials so treated have a durable flame retardance.

11 Claims, No Drawings

DURABLE FLAME RETARDANT FOR POLYESTER TEXTILE MATERIALS

SUMMARY OF THE INVENTION

Novel, phosphorous-containing flame retardants which impart durable flame retardant properties to polyester-containing textile materials when topically applied thereto are described. Also described are flame retardant textile materials comprised of polyester, cellulose, or blends thereof.

DESCRIPTION OF THE PRIOR ART

During the past several years, a large number of flame retardants have been developed for use with an almost equally large number of flammable materials. Cellulosic material (such as paper and wood) and polymeric materials (such as polyolefins, polyesters, polyurethane and polystyrene) are just two examples of materials for which flame retardants have been developed. For any class of flammable materials, such as, e.g., poly(ethylene terephthalate) polymers, some flame retardant additives are more effective than others. This is because the efficacy of any flame retardant in polymeric compositions is measured not only by the flame retardant capability of the additive but also by the ability of the additive to improve or modify—or at least not to detract from—other physical or mechanical properties of the polymer or polymeric composition. The mere fact that most flame retardants contain halogen and phosphorus atoms does not assure than any given halogenated or phosphorus-containing compound will impart usable flame retarding characteristics to any polymeric system. Many flame retardants will not impart usable flame retardancy to a polymeric system because they do not pyrolyze at the right temperature, they do not generate the appropriate free radicals during pyrolysis, they hold the polymeric system together during pyrolysis and prevent it from dripping, they migrate, they degrade during processing, etc.

There is a great interest in and a growing demand for flame retardant textiles and fabrics. However, the difficulties encountered in providing such a flame retardant textile material are enormous. The prior art has recognized the fact that various textile materials differ substantially in both flammability characteristics and physical properties.

A number of very substantial problems have been encountered by those who have attempted to incorporate a flame retardant into a polyester polymer prior to spinning. Many of the flame retardants so incorporated degraded during spinning because they were unable to withstand the very high temperatures needed for the extrusion of the polyester fiber. Many of said compounds reacted with the extruded fiber and adversely affected one or more of its properties. Many of said compounds reacted with various polymer additives, such as dye site additives, or with catalysts utilized during the preparation of the polymer. Oft times, the incorporation of the flame retardant into the polymer blend adversely affected the dyeability, the hand, the physical properties, or the processability of the fiber.

It is preferred to apply the flame retardant topically to the extruded fiber or the fabric. Such a process avoids the problems caused by thermal degradation of the flame retardant during spinning; and such a process cannot adversely affect the processability of the fiber. However, it is difficult to topically apply a flame retardant to polyester textile material so that it stays on the fiber after repeated washings. Topically applied flame retardants are generally not as durable as those which are incorporated into the polymer prior to spinning.

DISCUSSION OF THE PRIOR ART

The most relevant prior art of which applicants are aware is U.S. Pat. No. 4,049,617. This patent claims phosphorous compounds containing from one to three 1,3,2-dioxophosphorinane rings and at least one —$CH_2OH$ substituent.

DESCRIPTION OF THE INVENTION

In accordance with this invention, there is provided a compound of the formula

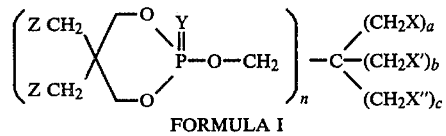

FORMULA I wherein each Z is independently selected from the group consisting of hydrogen and halogen; Y is oxygen or sulfur; n is an integer of from 1 to 3; a, b, and c are integers of from 0 to 1; $n+a+b+c=4$; and wherein X, X', X'' are independently selected from the group consisting of hydrogen, halogen, alkyl of 1 to about 8 carbon atoms and —OC(O)R, provided that at least one of said X, X', X'' substitutents is —OC(O)R, and R is independently selected from the group consisting of alkyl of 1 to about 18 carbon atoms, haloalkyl of 1 to about 18 carbon atoms, alkoxyalkyl of from 1 to about 18 carbon atoms, aryl of from 6 to about 18 carbon atoms, and haloaryl of from about 6 to about 18 carbon atoms.

The flame retardant compounds within the scope of this invention have the formula I above, wherein each Z is either hydrogen or halogen, preferably halogen. It is preferred that Z be chlorine or bromine. It is more preferred that Z be bromine.

In the compounds of this invention, said Y is either oxygen or sulfur. The oxygen compounds work well; their sulfologs are also operable.

In the compounds of this invention, n is an integer of from 1 to 3. a, b, and c are either 0 or 1, and $n+a+b+c=4$. X, X' and X'' are independently selected from the group consisting of hydrogen, fluorine, chlorine, bromine, iodine, alkyl of from 1 to about 8 carbon atoms, alkoxyalkyl of from 1 to about 8 carbon atoms, haloalkyl of from 1 to about 8 carbon atoms, and —OC(O)R. At least one of the X substituents is —OC(O)R. It is preferred that said alkyl, alkoxyalkyl, and haloalkyl substituents contain from about 1 to about 3 carbon atoms. It is preferred that said X, X', and X'' substituents be independently selected from the group consisting of hydrogen, halogen, and —OC(O)R. The preferred halogen substituent on the alkyl group is either chlorine or bromine, bromine being the most preferred constituent.

At least one of said X, X', and X'' substituents must be —OC(O)R. R is selected from the group consisting of alkyl of 1 to about 18 carbon atoms, alkolyalkyl of from 1 to about 18 carbon atoms, haloalkyl of from 1 to about 18 carbons, aryl of from about 6 to about 18 carbon atoms, and haloaryl of from about 6 to about 18 carbons. When R is an alkyl, alkoxyalkyl, or haloalkyl group, it is preferred that it contain from 1 to about 8 carbon atoms, preferrably 1 to about 3 carbon atoms. When R is an aryl or haloaryl group, it is preferred that it contain 6 carbon atoms.

The numerical designation used in naming the compounds within the scope of this invention can be ascertained with reference to the following formula where the numbers of the heterocyclic ring are numbered.

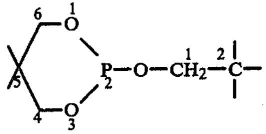

Representative compounds within the scope of the present invention include: 2(2',2'-Bis-bromoethyl-3'- octanoyl propoxy)-5,5-bis-bromomethyl-2-oxo-1,3,2-dioxaphosphorinane; 2(2',2'-Bis-bromomethyl-3'-acetylpropoxy)-5,5-bis-bromomethyl-2-oxo-1,3,2-dioxaphosphorinane; 2(2',2'-bis-bromomethyl-3'-proprionylpropoxy)-5,5-bis-bromomethyl-2-oxo-1,3,2-dioxaphosphorinane; 2(2',2'-bis-bromomethyl-3'-benzoylpropyxy)-5,5-bis-bromomethyl-2-oxo-1,3,2-dioxaphosphorinane; 2(2',2'-bis-bromomethyl-3'-chloroacetyl-propoxy)-5,5-bis-bromomethyl-2-oxo-1,3,2-dioxaphosphorinane; 2(2',2'-bis-bromomethyl-3'-tribromobenzoylpropoxyl)-5,5- bis-bromomethyl-2-oxo-1,3,2-dioxaphosphorinane; 2(2',2'-bis-bromomethyl-3'-acetylpropoxy)-5,5-dimethyl-2-oxo-1,3,2 dioxaphosphorinane; 2(2',2'-bis bromomethyl-3'-bromoacetylpropoxy)-5,5-dimethyl-2-oxo-1,3,2-dioxaphosphorinane; 0,0' bis (5,5,bis-bromomethyl-2-oxo-1,3,2-dioxaphosporanyl) 2,2 bis(-methyl acetyl) 1,3-dioxypropane; 2(2',2'-bis ethoxymethyl-3'acetylpropoxy)-5,5-bis-bromomethyl-2-oxo-1,3,2-dioxaphosphorinane; 2(2',2'-dimethyl-3' dichlorocecetyl-propoxy)-5,5-bis-bromomethyl-2-oxo-1,3,2-dioxaphosphorinane; 2(2'-ethyl-2'-methyl-3'-actylpropoxy)-5,5-bis bromomethyl-2-oxo-1,3,2-dioxaphosphorinane; and the like.

The compounds of this invention are hydrolytically stable. Their stability is demonstrated by a test wherein four grams of the compound is first completely emulsified with one gram of emulsifier and 45 grams of water and titrated with a standard potassium hydroxide solution; then another such emulsion is heated at 100° C. for 44 hours and then titrated. The "acid numbers" for the "aged" and "control" emulsions are the number of milligrams of potassium hydroxide (per gram of sample) used during the titration. The less the difference is between the "acid numbers" of the "aged" and "control" samples, the more hydrolytically stable the compound is. For the compounds of this invention, said difference range from about 0 to about 2.0 and, preferably, are less than about 0.5.

In addition to being hydrolytically stable, the compounds of this invention exhibit good thermal stability.

Some of the preferred compounds of this invention may be prepared by reacting a hydroxy-containing compound of the formula:

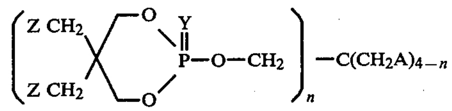

(wherein Z, Y and n are as hereinbefore described, and A is selected from the group consisting of hydrogen, halogen, and hydroxyl, provided that at least one of said A substituents is hydroxyl) with an acid anhydride of the formula

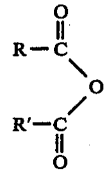

or alternatively, with an acid chloride of the formula

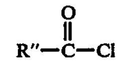

(wherein R, R', and R" are independently selected from the group consisting of alkoxyalkyl, alkyl, haloalkyl, aryl, or haloaryl). At least one mole of the acid anhydride or acid chloride must be present per mole of the phosphorus compound for a mono-hydroxy compound; at least two moles of the acid anhydride or the acid chloride must be present for a reaction with the dihydroxy phosphorus compound; at least three moles of either of these reactants must be present for a reaction with the tri-hydroxy compound. This type of esterification reaction is well known in the art.

Generally the reaction proceeds at a temperature of from about 90° to about 150° C. until all of the hydrogen chloride (in the case of the acid chloride reactant) or all of the carboxylic acid (in the case of the acid anhydride reactant) has been evolved. As chemists skilled in the art will readily recognize, the exact reaction conditions to be utilized in any one reaction will be functions of, inter alia, the reactivity and physical properties of the reactants utilized.

Some of the other preferred compounds of this invention may be prepared by reacting a chlorophosphate of the formula:

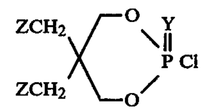

with an equimolar amount of an alcohol of the formula

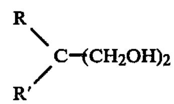

and thereafter esterifying the product. The starting materials which can be used to prepare these compounds are described in U.S. Pat. No. 4,049,617.

It is preferred that the compounds of this invention be soluble in at least one common organic solvent (such as xylene). Thus, at ambient temperatures, at least 10 percent of the compound of this invention is soluable in said solvent. It is preferred that at least 20 percent of the compound of this invention be soluble in said solvent at ambient temperatures.

Compounds of this invention may be used with polyester-containing textile materials such as polyester fiber and woven and non-woven fabrics containing at least 25 percent (by weight) of polyester. It is preferred that the textile material utilized in the instant invention contain at least 35 percent (by weight) of polyester; it is more preferred that said textile material contain at least 50 percent (by weight) of polyester. It is preferred that the polyester-containing textile materials treated by the compounds of this invention be comprised of a cellulosic fiber selected from the group consisting of cotton fiber, acetate fiber, and triacetate fiber.

The compounds of this invention may be applied to said polyester-containing textile materials by dissolving them in a commercial solvent such as xylene, running the polyester-containing fabric through the xylene solution, wringing excess solution from the fabric, heating the treated fabric to dry off excess solvent, and then curing the treated material to fix the flame retardant into the textile material. There are many ways of topically applying the flame retardant compound of this invention to polyester-containing textile materials; the "pad-dry-cure" method described herein is but one method which is well known in the art. In this method, generally, the compound of the instant invention is dissolved in a solvent such as xylene; however, many other solvents such as chloroform, methanol, acetone, toluene, mixed aromatic solvents, HiSol 10 (a solvent commercially available from the Ashland Oil Company), and the like can be used. The concentration of the flame retardant compound is from about 1 to about 25 percent (by weight); the preferred concentration is about 3 to about 20 percent (by weight), and the most preferred concentration is about 15 percent. After the fabric is run through the solvent solution, it is padded and subject to heat at a temperature of about 105° C. to flash off the solvent from the treated textile material. Thereafter it is dried at a temperature of from about 150° to 225° C. for from about 1 to 7 minutes in order to fix flame retardant into the textile material. Then it is scoured with commercially available afterwash solutions such as, e.g., a solution comprised of soda ash and of Triton QS44 (an alkali-stable, non-ionic surfactant). Other scouring solutions well known in the textile art may be used.

The compounds of this invention also work well when applied to triacetate textile materials. When the compounds of this invention are so utilized, they are applied in the dry spinning process. Such a process is described in detail in pages 107 et seq. of "Man-made Fibers," Vol. 2 (Interscience, New York, N.Y., 1968), the disclosure of which is hereby incorporated by reference. The flame retardant is incorporated into the spinning dope at a concentration of about 1 to about 50 percent (by weight) and spun by the conventional method taught by the prior art. This method generally utilizes lower processing temperatures than are used, e.g., during the spinning of polyester fibers.

It is preferred that the treated polyester, polyester/-cellulosic, or cellulosic textile material be comprised of from about 1 to about 25 percent of flame retardant by weight. It is more preferred that said textile material be comprised of from about 2 to about 20 percent (by weight) of flame retardant.

The following examples are provided for the purpose of further illustration only and are not intended to be limitations on the disclosed invention. Unless otherwise specified, all temperatures are in degress centigrade, all weights are in grams, and all volumes are in milliliters.

EXAMPLE 1

In substantial accordance with the procedure described in Example I of U.S. Pat. No. 4,049,617, 2(2',2'-bis bromomethyl)-3-hyroxypropyl-5,5-bis bromomethyl-2-oxo-1,3,2-dioxaphosphorinane was prepared.

EXAMPLE 2

Preparation of 2-(2',2'-bis bromomethyl-3'-acetylpropoxy-5,5 bis bromomethyl-2-oxo-1,3,2-dioxaphosphorinane.

Two hundred eighty-five grams of the compound of Example 1 were heated to 90° C. Fifty-three and one half grams of acetic anhydride were added incrementally to this compound with cooling at a temperature of 90°-95° C. over a period of about 20 minutes. The resulting mixture was then heated at 90° C. for about 1 hour. It was then initially washed with 300 milliliters of deionized water at 60° C. for about 30 minutes. Thereafter, it was washed three times each time at 60° C. with 300 milliliters of deionized water to which aqueous ammonia had been added to keep the pH at from about 7 to about 8. After the final wash, the product was dried under vacuum to give 279 grams of a viscous liquid with an acid number of less than 0.5. Elemental analysis indicated that the compound contained 52.4 percent bromine. The calculated bromine content of this compound was 52.4 percent.

EXAMPLE 3

Preparation of 2-(2',2'-Bis-bromomethyl-3'-proprionylpropoxy)-5,5-bis-bromomethyl-2-oxo-1,3,2-dioxaphosphorinane.

Nine Hundred and eleven grams of the compound of Example 1, 900 ml of toluene, and 148 grams of propionyl chloride were heated to a temperature of 70° C. for 1 hour. Thereafter, 600 ml. of toluene were added to the reaction mixture, and the reaction was continued for another 30 minutes at 70° C. The contents were then heated to 85° C. for about 30 minutes and then refluxed for about 1.5 hours. The toluene was removed under reduced pressure to give a low melting solid. Elemental analyses indicated that the compound contained 50.89 percent bromine. The calculated bromine content for this compound was 51.2 percent. This compound was thermally stable, losing only 5 percent of its weight at 255° C. when tested on the DuPont 990 Thermal Analyzer.

EXAMPLE 4

Preparation of 2-(2',2'-Bis-bromomethyl-3'-octanoylpropoxy)-5,5-bis-bromomethyl-2-oxo-1,3,2-dioxaphosphorinane.

Two hundred and fifty grams of the compound of Example 1, 700 ml. of toluene, and 71.6 gms of octanoyl chloride were heated to a temperature of 80° C. for about one hour and then refluxed for about 90 minutes. The solution was then washed twice with 700 ml of deionized water to which aqueous ammonia had been added to bring the pH to from about 7 to about 8. A final wash with deionized water with a pH adjustment was given. The product, a low melting solid, was then recovered from toluene.

EXAMPLE 5

A 20 percent solution of the compound of Example 2 in xylene was prepared. A 100 percent poly(ethylene terephthalate) fabric (which had been manufactured by Test Fabrics, Inc., Style 755), was passed through this solution, padded to a wet pickup of about 73.5 percent and air dried. The dried fabric sample was cured about 90 seconds at a temperature of 200° C. and thereafter was afterwashed in a solution containing about 0.1 percent sodium carbonate and about 0.05 percent Triton QS34 (an alkali-stable, non-ionic surfactant). Thereafter the fabric was rinsed and tumble dried. Samples of this fabric, samples of a control untreated fabric, and samples of this fabric which had been laundered through 50 Heltra launderings and drying cycles were tested for flammability by a vertical burn test in which the specimens had a double zig-zag stitch of polyester thread treated with a silicone finish sewn up its middle. An airless methane gas flame was impinged on the stitching of the treated sample and of that of an untreated, control sample, for 3 seconds; the resulting char lengths were measured.

The untreated control specimens burned their entire length, both at time zero and after 50 launderings when tested in accordance with the procedure of this example. The treated test specimens, which were 10 inches long, burned 2.6 inches at time zero and 3.8 inches after 50 laundering cycles.

EXAMPLE 6

In substantial accordance with the procedure of Example 5 poly(ethylene terephthalate) fabric was treated with a 20 percent xylene solution of the compound of Example 3. In the flammability testing, the untreated control specimens burned their entire lengths both at time zero and after 50 launderings, when tested in accordance with the procedure of Example 5. The treated specimens burned 3.2 inches at time zero and 3.6 inches after 50 launderings.

EXAMPLE 7

A mixture of 20 parts of the compound of Example 1 (by weight) and 80 parts of xylene (by weight) is prepared. When this mixture is applied to polyester fabric in substantial accordance with the procedure described in Example 5 and the treated fabric is dried, cured, scoured, and tested for flammability in accordance with said procedure, the treated fabric burns its entire length at "time zero."

EXAMPLE 8

The oxygen indices of the treated fabrics of Example 5 and 6 were determined in accordance with ASTM Test D-2863-74. The untreated poly(ethylene terephthalate) fabric had an oxygen index of 23.5, the treated polyester fabric of Example 5 had an oxygen index of 27. The treated fabric of Example 6 had an oxygen index of 30.

The compounds of this invention have many other applications besides those described hereinabove which are readily obvious to those skilled in the art. Thus, e.g., they can readily be used to flame retard all forms of polyurethanes, they can be used to flame retard foamed polystyrene, they can be used to flame retard polypropolene fiber, and they can be used to flame retard poly(ethylene terephthalate) fiber, etc.

The embodiments of the invention in which an exclusive property or privilege is claimed are defined as follows:

1. A compound of the formula

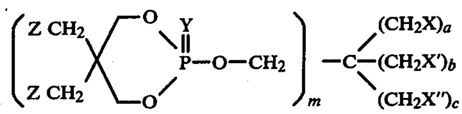

wherein each Z is independently selected from the group consisting of hydrogen and halogen; Y is oxygen or sulfur; n is an integer of from 1 to 3; a, b, and c are integers of from 0 to 1; n+a+b+c= 4; and wherein X, X', X" are independently selected from the group consisting of hydrogen, halogen, alkyl of 1 to about 8 carbon atoms and —OC(O)R, provided that at least one of said X, X', X" substituents is —OC(O)R, and R is independently selected from the group consisting of alkyl of 1 to about 18 carbon atoms, haloalkyl of 1 to about 18 carbon atoms, alkoxyalkyl of from 1 to about 18 carbon atoms, aryl of from 6 to about 18 carbon atoms, and haloaryl of from about 6 to about 18 carbon atoms.

2. A compound of the formula

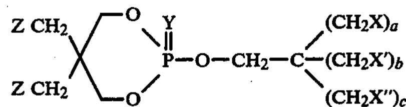

wherein each Z is independently selected from the group consisting of hydrogen and halogen; Y is oxygen or sulfur; a, b, and c are integers of from 0 to 1; and X, X', and X" are independently selected from the group consisting of hydrogen, halogen, alkyl of 1 to about 8 carbon atoms and —OC(O)R; provided that at least one of said X, X', X" substituents is —OC(O)R, and R is independently selected from the group consisting of alkyl of 1 to about 18 carbon atoms, haloalkyl of 1 to about 18 carbon atoms, alkoxyalkyl of from 1 to about 18 carbon atoms, aryl of from 6 to about 18 carbon atoms, and haloaryl of from about 6 to about 18 carbon atoms.

3. A compound of the formula

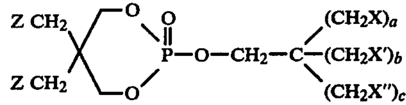

wherein Z is halogen; a, b, and c are integers of from 0 to 1; and X, X', and X" are independently selected from the group consisting of hydrogen, halogen, and —OC(O)R wherein R is alkyl of 1 to about 8 carbon atoms, provided that at least one of said X, X', and X" substituents is —OC(O)R.

4. The compound of claim 2, wherein X, X', and X" are independently selected from the group consisting of hydrogen, halogen, and —OC(O)R.

5. The compound of claim 3, wherein said halogen is selected from the group consisting of bromine and chlorine.

6. The compound of claim 5, wherein Z, X' and X" are bromine, and X is —OC(O)R.

7. The compound of claim 6, wherein R is $—CH_3$.

8. The compound of claim 6, wherein R is $—C_2H_5$.

9. The compound of claim 6, wherein R is $—C_7H_{15}$.

10. The compound of claim 6, wherein R is $—C_3H_7$.

11. A flame-retarded textile material containing at least 25 percent (by weight) of polyester and an effective amount of the compound of claim 3.

* * * * *